United States Patent
Collins et al.

(10) Patent No.: US 7,306,736 B2
(45) Date of Patent: Dec. 11, 2007

(54) VALVE MECHANISM FOR INFUSION FLUID SYSTEMS

(75) Inventors: Gregory R Collins, Monroe, NY (US); James Summerton, Hillsdale, NJ (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 303 days.

(21) Appl. No.: 10/433,845

(22) PCT Filed: Dec. 7, 2001

(86) PCT No.: PCT/US01/47211

§ 371 (c)(1),
(2), (4) Date: Oct. 27, 2003

(87) PCT Pub. No.: WO02/45813

PCT Pub. Date: Jun. 13, 2002

(65) Prior Publication Data

US 2004/0089594 A1 May 13, 2004

Related U.S. Application Data (60) Provisional application No. 60/254,230, filed on Dec. 8, 2000.

(51) Int. Cl.
*B01D 61/26* (2006.01)
*B01D 61/30* (2006.01)

(52) U.S. Cl. ............ 210/646; 210/87; 210/97; 210/101; 210/103; 210/134; 210/136; 210/321.6; 210/741; 604/5.01; 604/6.09

(58) Field of Classification Search ............ 210/85–87, 210/90, 97, 103, 104, 109, 117, 134, 136, 210/137, 143, 195.2, 257.2, 645, 646, 739, 210/741, 805, 806, 101, 321.6; 604/5.01, 604/6.09

See application file for complete search history.

(56) References Cited

U.S. PATENT DOCUMENTS 4,702,829 A 10/1987 Polaschegg et al.

(Continued)

FOREIGN PATENT DOCUMENTS

| JP | H63-145664 | 6/1988 |
| JP | H63249570 | 10/1988 |
| JP | H01-303155 | 12/1989 |
| JP | H02116453 | 9/1990 |

(Continued)

OTHER PUBLICATIONS

European Search Report for PCT/US01/47211.
International Search Report.

*Primary Examiner*—Joseph Drodge
(74) *Attorney, Agent, or Firm*—Darby & Darby (57) ABSTRACT

A method and an apparatus are provided for preventing retrograde flow of fluid, e.g., blood products, into a source of sterile substitution fluid (50). The apparatus of the present invention includes a controllable pinch valve member (110) that is placed on a section of a conduit (90) which carries sterile substitution fluid to an extracorporeal circuit (30). In one embodiment, control over the valve member (110) is based on a control unit (120) using fluid pressures that are sensed upstream and downstream of the valve member (110) by upstream sensor (121) and downstream pressure (122) respectively. The valve member (110) is preferably opened only when the upstream pressure is greater than the downstream pressure. This assures that the substitution fluid flows only in a single direction when the pinch valve member (110) completely occludes the conduit (90) when in a closed position. Therefor, blood will not contaminate the sterile fluid by being drawn into the conduit (90) due to pressure differences.

18 Claims, 3 Drawing Sheets

U.S. PATENT DOCUMENTS

| | | |
|---|---|---|
| 4,765,888 A | 8/1988 | Barthe et al. |
| 4,846,787 A | 7/1989 | Aall-Flood et al. |
| 5,366,630 A | 11/1994 | Chevallet et al. |
| 5,624,551 A | 4/1997 | Baumann et al. |
| 5,808,181 A | 9/1998 | Wamsiedler et al. |
| 5,846,419 A | 12/1998 | Nederlof |
| 5,852,231 A * | 12/1998 | Kaji ........................ 73/61.56 |
| 6,303,036 B1 * | 10/2001 | Collins et al. .............. 210/646 |
| 6,423,231 B1 * | 7/2002 | Collins et al. .............. 210/646 |

FOREIGN PATENT DOCUMENTS

| | | |
|---|---|---|
| JP | H05-192399 | 8/1993 |
| JP | H07-299133 | 11/1995 |
| JP | H09-164198 | 6/1997 |
| JP | 3069839 | 4/2000 |
| WO | PCT/US99/17468 | 2/2000 |
| WO | PCT/US99/25804 | 5/2000 |

* cited by examiner

FIG. 3

VALVE MECHANISM FOR INFUSION FLUID SYSTEMS

CROSS-REFERENCE TO RELATED APPLICATION

This is a U.S. national phase application under 35 U.S.C. §371 of International patent application Serial No. PCT/US01/47211 filed Dec. 7, 2001 and claims the benefit of U.S. provisional application Ser. No. 60/254,230, filed Dec. 8, 2000, which is hereby incorporated by reference in its entirety. The International Application was published in English on Jun. 13, 2002 as WO 02/45813 A1 under PCT Article 21(2).

FIELD OF THE INVENTION

The present invention relates to the production of and supply of sterile fluids in general and, more particularly, to a valve mechanism intended to be used with current systems which deliver sterile fluid from an external source or from a fluid preparation section of a machine to a point of use, such as a blood and fluid mixing chamber.

BACKGROUND OF INVENTION

Therapies, including hemofiltration, hemodiafiltration, and plasma pheresis, that require significant volumes of plasma water to be filtered and discarded require an equal or slightly smaller volume of fresh replacement fluid to be directly or indirectly infused into the patient's vascular compartment. In hemodialysis, for example, the infusion fluid is generally used to prime an extracorporeal circuit of a blood-cleansing machine, prior to connecting a patient to the machine, and to rinse the patient's blood at the end of the treatment. In the practice of hemodiafiltration, plasma water is removed by filtration from the blood as it traverses through the hemodialyzer cartridge. To compensate for this loss of plasma water, sterile fluid is added either upstream or downstream of the dialyzer cartridge. The sterile fluid used in these applications is generally a normal saline solution (e.g., a solution having a sodium chloride concentration of 0.9 percent by weight) which is supplied in flexible bags having predetermined volumes. In some cases, a Ringer's Lactate Solution may be used. In peritoneal dialysis, sterile peritoneal dialysis fluid packaged in flexible bags is typically infused into and subsequently emptied from the patient's peritoneal cavity.

The current state of the art employs one of two basic schemes for meeting the replacement infusion fluid requirements of such treatments. A commercially prepared solution intended for intravenous infusion is contained in a suitable reservoir, such as a flexible bag or a non-flexible vented bottle. The reservoir is connected to a fluid delivery assembly that includes a pump, such as a peristaltic pump and sterile tubing with appropriate connectors. The pump is used to create the required pressure differential between the fluid reservoir and a point of use (e.g., a blood and fluid mixing chamber) to assure the infusion fluid flow moves in a direction toward the point of use.

If an occlusive type pump is used, such as a peristaltic pump, an additional function of the pump is to assure that there is no retrograde flow of the patient's blood back into the sterile fluid reservoir. Due to pressure pulsations caused by the peristaltic pump, some retrograde flow of blood into the sterile tubing set occurs. Because of this, the sterile tubing set is disposed at the end of the treatment. Typically, in this arrangement, the sterile tubing set contains a special pump segment sized for the peristaltic pump. This results in a greater cost when compared to using a standard intravenous (IV) administration set.

A second strategy employed when larger volumes of fluid are required is to proportion water and salts to produce a solution that is similar in ionic content to plasma water as done by a dialysis machine to make dialysate. In this configuration, the dialysate solution or a portion of the solution must be treated (such as by filtration) to ensure it is of injectable quality prior to being used as a replacement or infusion fluid. Typically, a pump, such as a gear pump, peristaltic pump or piston pump is used to create the pressures required to move the required volume of fluid through the sterilizing filter(s) and to the point of use. Various articles describe many configurations of the substitution pump relative to the sterilizing filters in online hemodiafiltration systems. For example, in U.S. Pat. No. 4,702,829 ('829), to Polaschegg et al., which is incorporated herein by reference, the substitution pump is placed between two (redundant) sterilizing filters. The object of the '829 apparatus is to minimize the amount of negative pressure that would potentially occur if the pump were placed on the downstream side of the two sterilizing filters. In addition, this configuration allows the first filter to be operated in a cross-flow mode. The '829 patent does not address any means of preventing the final sterilizing filter (located between the venous drip chamber and the substitution pump) from being contaminated by blood products (red cells, proteins, etc.). For example, it is very common for blood to back-up in the drip chambers when pressures build up, such as when a blood line becomes kinked downstream of the drip chamber.

Though the infusion tubing segment between the final filter and the venous chamber may include a microfilter (e.g., 0.22 micron nominal pore size), it is understood by those skilled in the art that this microfilter does not prevent the final sterility filter from being contaminated by blood proteins when blood backs up into the infusion tubing set that is attached to the final sterility filter. Thus, it is implied that one would need to disinfect or sterilize the apparatus, including the final sterilization filter, before a new treatment is performed on the next patient.

In an article by Canaud, B. et al., "*Hemodiafiltration Using Dialysate as Substitution Fluid*", Artificial Organs, Vol. 11(2), pp. 188-190, which is incorporated herein by reference, two different configurations are shown. In one configuration, the substitution pump is located before the two redundant sterilizing filters, while in the other configuration, the substitution pump is located between the two filters similar to that described in the '829 patent. The article fails to elaborate or teach the function of a stop valve which is shown in one of the figures. In addition, the article states that the machine and the infusate circuit is disinfected twice a day with perchloric acid and sterilized at the end of each day with 2.5 formalin. This implies that it is necessary to perform a disinfection process that includes the machine and the sterility filters between treatments in order to assure no cross contamination occurs between patients treated serially with the same system.

In U.S. Pat. No. 5,846,419 ('419) to Nederlof, which is incorporated herein by reference, two configurations are described. One configuration has the substitution pump between two sterilizing filters, while a second configuration has the substitution pump between the final sterilizing filter and the bloodline drip chamber. The '419 patent is directed to a method for preventing accumulation of germs and pyrogens on the upstream side of the sterility filters by enabling them to be operated in a cross-flow mode during treatment with these systems. The patent does not consider contamination of the downstream side of the final sterility filter such that can occur when blood backs up in the drip chamber shown in the figures of the patent.

In addition, there are several dialysis/diafiltration machines on the market that generate substitution fluid online using dialysate. In one system, the substitution pump is located between a second and third ultrafiltration or sterility filter. The third (final) sterility filter is part of the infusion set, thus the infusion set and final sterility filter is used only once to prevent any cross contamination. This type of system is embodied in a product commercially distributed under the trade name Gambro AK 200 Ultra™, from Gambro AB of Lund Sweden.

In a second system, the substitution pump is located after the final sterility filter. Because this system uses an occluding type (peristaltic) pump, it assures that no blood products will back up into the sterilizing filters. Therefore, disinfecting between treatments may not be required. The disadvantage of this system is that the system requires a special infusion tubing set that includes a dedicated pump segment for its operation. This infusion tubing set is accordingly more complex and costly than a standard IV administration set (that is typically used to prime the circuit with saline or for infusing sterile fluid into the blood circuit during dialysis treatment). Again, to prevent cross contamination, this special infusion tubing set is used once and is then discarded. An example of this type of system is a product system commercially available under the trade name Fresenius OnLine Plus™ System, available from Fresenius Medical Care of Bad Homburg, Germany.

SUMMARY OF INVENTION

The present invention provides a method and an apparatus that prevents retrograde flow of fluid, e.g., blood products (i.e., blood proteins), into a source of sterile substitution fluid. The apparatus of the present invention includes a controllable valve mechanism having a valve member that is placed on a section of a conduit which carries sterile substitution fluid to an extracorporeal circuit. In one embodiment, the controllable valve member is in the form of a pinch valve which is placed along a section of flexible tubing. Control over the pinch valve is based on a control unit, e.g., a feedback control loop, using fluid pressures that are sensed upstream and downstream of the pinch valve. The pinch valve is preferably opened only when the upstream pressure is greater than the downstream pressure. This assures that the substitution fluid flows only in a single direction (i.e. from the higher pressure substitution fluid source to the lower pressure extracorporeal circuit) when the pinch valve is in the open position.

Because the pinch valve completely occludes the conduit (flexible tubing) when in the closed position, blood (and its associated blood proteins) will not contaminate the sterile fluid delivery system upstream of the pinch valve by being drawn into the flexible tubing due to pressure differences. As a result, this enables the sterile fluid delivery system (excluding the flexible tubing contained in the pinch valve) to be used multiple times on multiple patients without disinfection of the fluid delivery system between treatments. The valve mechanism of the present invention thus overcomes the disadvantages of the conventional devices because it greatly reduces costs associated with disinfecting the sterile fluid delivery system, not to mention the lost time associated with having to disinfect the system between each treatment.

For those systems using an occlusive type substitution fluid pump requiring a special single use infusion set (which may contain a single use final sterilizing filter), the present invention has the advantage in that a low cost IV administration set or a drip chamber level adjust line on an existing bloodline set can be used instead.

According to the present invention, the valve mechanism may be incorporated into a system in which sterile substitution fluid is introduced into the blood stream either in a pre-dilution mode or in a post-dilution mode relative to a dialyzer cartridge. In addition, the valve mechanism may also be incorporated into a hemodiafiltration scheme using first and second dialyzer cartridges. In this embodiment, the substitution fluid is introduced into a partially diafiltered blood stream at a location between the first and second dialyzer cartridges.

Other features and advantages of the present invention will be apparent from the following detailed description when read in conjunction with the accompanying drawings.

DETAILED DESCRIPTION OF PREFERRED EMBODIMENTS

Figure 1:
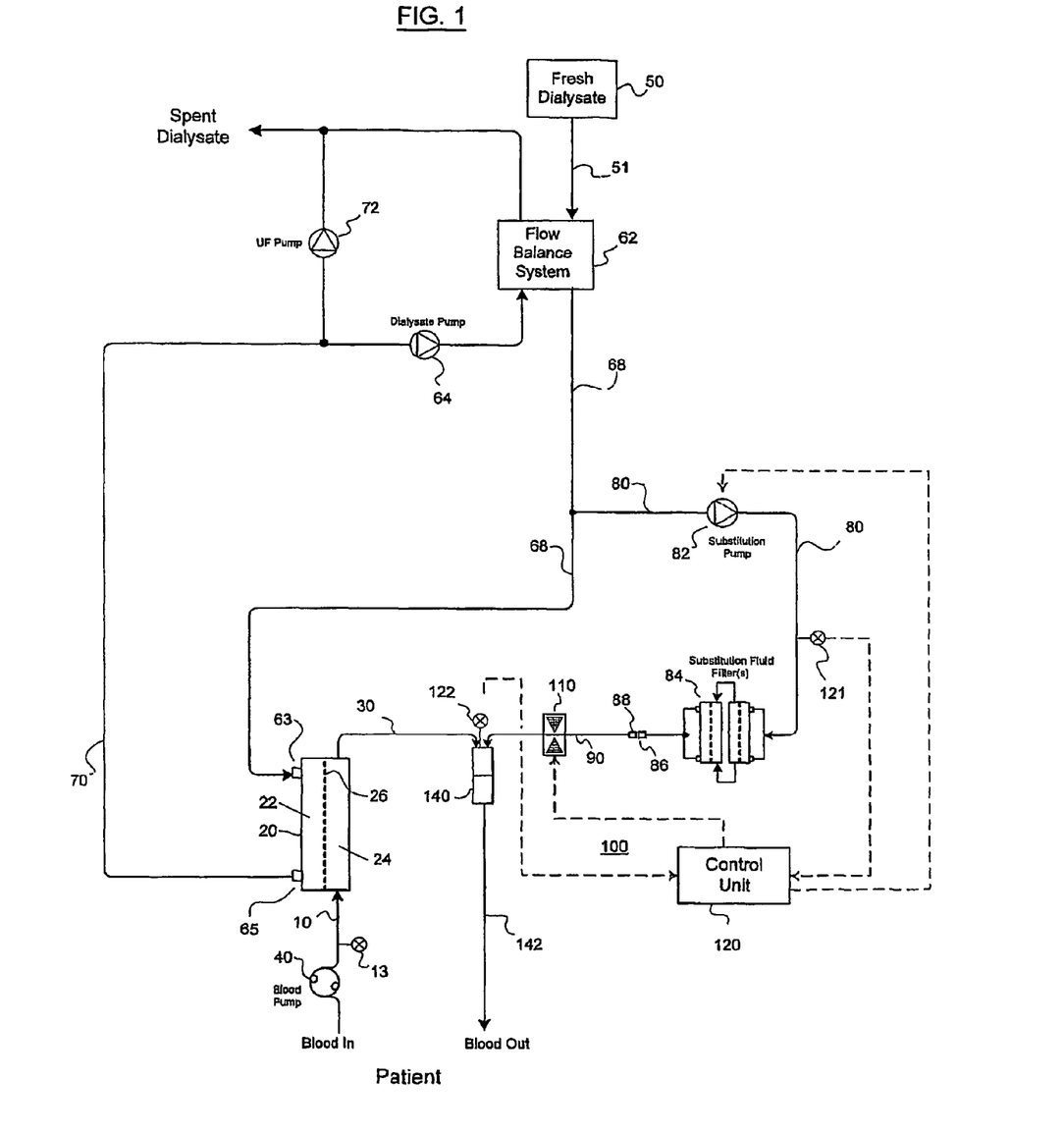
FIG. 1 is a schematic illustration of a fluid sterilization system incorporating a valve mechanism in accordance with a first embodiment.

Reference is made to FIG. 1 which schematically illustrates a first embodiment. In this first embodiment, the present scheme is shown as being part of a substitution fluid delivery system typical of a hemodiafiltration system with online substitution fluid. The embodiment of FIG. 1 illustrates a hemodiafiltration scheme in which the substitution fluid is introduced into the blood stream in a post-dilution mode. Blood from a patient enters an extracorporeal circuit. The extracorporeal circuit generally includes an arterial bloodline 10, a dialyzer cartridge 20 having a dialysate compartment 22 and a blood compartment 24, and a venous bloodline 30. The dialyzer cartridge 20 includes a semipermeable membrane 26 which divides the cartridge 20 into the compartments 22, 24. Pressures in the extracorporeal circuit are typically monitored, as represented by arterial pressure at a first monitoring device 13 and venous pressure at a second monitoring device 122. The first and second monitoring devices 13, 122 may be in the form of any number of devices and in one exemplary embodiment, the devices 13, 122 are pressure sensors which detect fluid pressure at these locations.

According to this embodiment, the dialyzer cartridge 20 preferably is a medium or high flux dialyzer, for example, Fresenius hemodialyzers F40, F50, F60, F70, F80, F60M, F80M, available from Fresenius Medical Care of Bad Homburg, Germany; Baxter hemodialyzers CT 110G, CT 190G and Atraflux 140, 170, 200, available from Baxter of Deerfield, Ill.; and Hospal AN69 hemodialyzers Filtral 12, 16, 20, available from Hospal of Meyzieu, France. Any suitable bloodline material known in the art may be used to carry the fluids in the system of the present invention. Examples include but are not limited to MediSystems Ready Set bloodlines, available from MediSystems of Seattle, Wash., and Fresenius Medical Care bloodlines, available from Fresenius Medical Care of Bad Homburg, Germany.

Blood is propelled through the extracorporeal circuit using a blood pump 40. Preferably, the blood is propelled in a counter-current configuration relative to the flow of a dialysate solution in the dialysate compartment 22. A dialysate fluid circuit is provided for preparing a source of fresh dialysate, generally indicated at 50. For example, the fresh dialysate 50 may be prepared by volumetric proportioning, e.g., mixing volumes of fresh water with dialysate concentrate at predetermined proportions, resulting in dialysate fluid 50 that is compatible with human blood but may not be sterile and may not be non-pyrogenic at this point. The dialysate fluid circuit also includes a flow balance system 62 (e.g., balance chambers) which may be used to prepare the dialysate fluid 50 having the predetermined desired properties. Fresh dialysate flows from the fresh source 50 through a first conduit 51 to the flow balance system 62.

A dialysate pump 64 is used to propel the dialysate fluid 50 through the dialysate fluid circuit which also includes a fresh dialysate conduit 68 for carrying fresh dialysate fluid 50 from the flow balance system 62 to the cartridge 20 and a spent dialysate conduit 70 for carrying spent dialysate fluid from a dialysate outlet port 65 of the cartridge 20. The dialysate conduit 70 is connected between the cartridge 20 and the flow balance system 62. A UF pump 72 is generally used to shunt a portion of spent dialysate fluid from the flow balance system 62 as a means to remove a controlled amount of fluid from the patient.

According to this embodiment, to make substitution fluid online, a portion of the fresh dialysate fluid 50 is drawn into a substitution fluid conduit 80. This can be accomplished using several different techniques including using a substitution pump 82 for pumping a portion of fluid 50 into the substitution fluid conduit 80 from the fresh dialysate conduit 68. In order to make fresh dialysate fluid 50 of an injectable quality, the fluid 50 may be filtered through a substitution filter unit 84. The substitution filter unit 84 may include one or more substitution fluid filters used to filter the fresh dialysate fluid 50 according to the present invention. The substitution filter unit 84 may include any filtration membrane known in the art and may be similar in composition to the membrane 26 used in hemodialyzers, such as dialyzer cartridge 20. However, preferably, the molecular weight cut-off of the filtration membrane is smaller than that of typical high flux dialyzers, whereby a better retention of endotoxin fragments, etc. is achieved. A desirable range of the molecular weight cut-off for the filtration membrane may be from about 5,000 to about 30,000 Daltons.

Although it is possible to use a substitution filter unit 84 having a single filtration stage (i.e. without redundant filtration) as the final filtration, preferably, the substitution filter unit 84 has redundant filtration characteristics. Accordingly, it is preferred that the substitution filter unit 84 has redundant filtration sections to assure the sterility of the filtered fluid in the event that one of the filters fails during the filtration process, as is known in the art. For example, the substitution filter unit 84 may consist of two single filter cartridges, or it may be designed as a single cartridge unit having multiple filtration sections. Thus while it is possible to use a single filtration phase (i.e. without redundant filtration) as a final filtration unit, it is generally undesirable due to patient safety issues that may arise should the filter fail during operation. Redundant filtration is thus generally required by industry standards.

The dialysate path in the embodiment of FIG. 1 may be arranged as follows. The fresh dialysate conduit 68 extends from the flow balance system 62 to a dialysate inlet port 63 of dialyzer cartridge 20 so that a portion of the fresh dialysate fluid 50 is delivered to the dialyzer cartridge 20. As previously-mentioned, a portion of the fresh dialysate fluid 50 is used to make substitution fluid online and flows from the fresh dialysate conduit 68 to the substitution filter unit 84 through the conduit 80. After the dialysate fluid passes through the substitution filter unit 84, the sterile substitution fluid is delivered to a suitable connector 86 which mates with another connector 88 that is part of a conduit 90 that leads to the extracorporeal circuit. In one embodiment, the conduit 90 is flexible tubing extending between the connector 88 and the extracorporeal circuit. The flexible tubing 90 may be considered the single use or disposable section of the infusion line pathway. For example, it may be part of a portion of a bloodline, such as a drip chamber level adjust line (as shown in FIG. 1), or an IV administration set connected to a suitable port in the extracorporeal circuit (e.g., drip chamber level adjust line, saline line tee, or special infusion port made as part of the hemodialyzer, hemodiafilter, or hemofiltration cartridge).

According to the present invention, a valve mechanism is provided and generally indicated at 100. The valve mechanism 100 is designed to prevent retrograde flow of blood products (e.g., blood proteins) into the source of sterile substitution fluid (substitution fluid that has passed through the substitution filter unit 84). In one embodiment, the valve mechanism 100 includes a main control valve 110 (e.g., a tubing pinch valve) and a control unit 120 that commands the main control valve 110 to open or close. The pinch valve 110 may be located in several different locations including on the flexible tubing 90 that is either an integral part of the bloodline tubing set (such as the drip chamber level adjust line) or is connected to the extracorporeal circuit (such as an IV administration set). The pinch valve 110 may be any number of suitable pinch valve mechanisms and in one embodiment the pinch valve 110 is a Sari pinch valve available from Farmington Engineering Inc., Madison, Conn. The pinch valve 110 fully occludes the flexible tubing 90 in the "closed" position and allows flow through the flexible tubing 90 in the "open" position. It will also be understood that it is within the scope of the present invention that the main control valve 110 is not limited to a pinch valve and may comprise other types of valve assemblies which serve to selectively occlude the flexible tubing 90 in the "closed" position and allow flow through the flexible tubing 90 in the "open" position. Other type of valves that can be used are those valves that are configured to occlude and conversely open the flexible tubing 90 when a signal or the like is sent to the valve from a programmable control unit, such as control unit 120, a microprocessor device, etc.

In accordance with one embodiment of the present invention (FIG. 1), control of the pinch valve 110 is based on fluid pressures (directly or indirectly) sensed before and after the pinch valve 110. In other words, the fluid pressure is measured at a location upstream of the pinch valve 110 and at a location downstream of the pinch valve 110. The sensing of the fluid pressures upstream and downstream of the pinch valve 110 may be accomplished by a third monitoring device 121 (i.e. an upstream sensor) and the second monitoring device 122 (i.e. a downstream sensor), respectively. For example and according to one embodiment, the upstream sensor 121 is an upstream pressure transducer 121 and the downstream sensor 122 is a downstream pressure transducer 122. Preferably, the venous pressure is also monitored at location 122, as previously indicated. The upstream side of the pinch valve 110 includes the substitution equipment which extends from the substitution pump 82 to the pinch valve 110. The downstream side of the pinch valve 110 includes both the extracorporeal circuit and the portion of the flexible tubing 90 which extends from the pinch valve 110 to the extracorporeal circuit. It will be appreciated that other types of sensing devices may be used to sense the fluid pressure in both the upstream and downstream locations. The fluid pressure is continuously monitored by the upstream sensor 121 and the downstream sensor 122. Control of the pinch valve 110 is thus based on a feedback control loop (control unit 120) which is designed to position the pinch valve 110 in either the open or closed position based upon the sensed information received from the sensors 121, 122. Control unit 120 is preferably a programmable unit that permits the operator/user to program selected pressure differentials that will trigger the control unit 120 to vary the position of the valve 110.

According to the present invention, control of the pinch valve 110 is as follows. When the pinch valve 110 is in a "closed" position (and assuming the substitution pump 82 is stopped), the pressure on the upstream side of the pinch valve 110 could be less than the pressure on the downstream side of the pinch valve 110. The opening of the pinch valve 110 under these conditions could result in blood flowing from the extracorporeal circuit toward the sterile source of substitution fluid. This is referred to as retrograde blood flow and the occurrence of which is undesirable as outlined in the discussion of the disadvantages of conventional systems. To initiate the flow of substitution fluid, the substitution fluid pump 82 is started with the pinch valve 110 remaining in the "closed" position. In this configuration, pressure on the upstream side of the pinch valve 110 will increase. When the sensed upstream pressure at sensor 121 exceeds the sensed downstream pressure at sensor 122 by some predetermined value, the pinch valve 110 is opened. The control unit 120 opens the pinch valve 110 by known techniques, such as sending a command signal to the pinch valve 110 (that is in communication with the control unit 120).

The opening of the pinch valve 110 permits flow of substitution fluid to the extracorporeal circuit. While the pinch valve 110 is in the "open" position, upstream and downstream pressures are continuously monitored at sensors 121, 122 to assure that the upstream pressure is greater than the downstream pressure. This information is thus continuously relayed from the sensors 121, 122 to the control unit 120. In the event that there is a sudden drop in the upstream pressure or a sudden increase in the downstream pressure, the pinch valve 110 is immediately closed to prevent blood and blood proteins from backing up and contaminating the substitution fluid delivery system. After the pinch valve 110 is closed, the substitution pump 82 is stopped to prevent over pressurizing the fluid path between the outlet of the substitution pump 82 and the pinch valve 110. This can be accomplished by sending a signal from the control unit 120 to the substitution pump 82.

An alternative to the feedback control scheme described above which is based on inputs of both upstream and downstream pressures is a feedback control scheme based only on the upstream pressure (i.e., as detected at an upstream location, such as at sensor 121). In this control scheme, the downstream pressure would be assigned a constant value that represents a maximum pressure condition based upon a predetermined set of treatment parameters (e.g., flows, filters, dialyzer cartridge, etc.). Operation of the valve mechanism 100 then becomes similar to that described above except that the control unit 120 only receives input from the sensed upstream pressure at sensor 121 and the control unit 120 includes a comparator or the like to compare the upstream pressure and the constant value. In this case, to initiate flow of substitution fluid after the substitution pump 82 is started, the pinch valve 110 will not open until the sensed upstream pressure at sensor 121 exceeds the downstream constant pressure value by some predetermined value. After the pinch valve 110 is opened, the control unit 120 can begin to monitor the upstream pressure for sudden changes. For example, a sudden drop in the upstream pressure results in the closing of the pinch valve 110 to prevent blood and blood proteins from backing up and contaminating the substitution delivery system followed by a stopping of the substitution pump 82. Again, the observed change in pressure at the upstream location that causes the opening or closing of the pinch valve 110 can be defined in a number of different ways. For example, the pressure change can be defined as the upstream pressure value exceeding the constant pressure value by a predetermined percentage or by the upstream pressure value being less than the constant pressure value by a predetermined percentage.

Yet another alternative arrangement is one in which the sensor 122 is still a downstream pressure sensor, or the like; however, the sensor 122 in this embodiment is positioned along the length of a downstream portion of conduit 90 downstream of the valve 110. Thus, the downstream pressure sensor 122 monitors the flow pressure of the substitution fluid as it flows within the conduit 90 after flowing through the valve 110 and before the substitution fluid is delivered to its point of use, i.e., mixing chamber 140 in the embodiment of FIG. 1. Thus in this embodiment, both the first and second sensors 121, 122 monitor the flow pressure of the substitution fluid with the sensor 121 monitoring an upstream flow pressure and the sensor 122 monitoring a downstream flow pressure. The control unit 120 in this embodiment operates in essentially the same manner as the valve 110 is opened and closed based on information received from the sensors 121, 122.

Because the present invention prevents retrograde blood flow, the substitution delivery system does not need to be disinfected before a next treatment is initiated. This greatly reduces the costs associated with the treatment and also saves valuable time as th system may be reused without having to undergo a time consuming cleaning process.

According to the present invention, a pressure based valve mechanism 100 is provided to eliminate the risk of system contamination due to retrograde blood flow into the sterile substitution fluid source. The principal reason retrograde blood flow occurs is that a pressure imbalance occurs and the downstream fluid pressure (i.e., near 122) is greater than the upstream fluid pressure (i.e., near 121). This results in the blood flowing from a location where the blood is mixed with sterile dialysate fluid, such as in a drip chamber or a mixing chamber 140, toward the source of the substitution fluid. The mixing chamber 140 is fluidly connected to the flexible tubing 90 which carries the sterilized substitution fluid to the mixing chamber 140 and is also fluidly connected to the dialyzer cartridge 20 by venous bloodline 30 for receiving filtered blood from the dialyzer cartridge 20. A conduit 142 delivers the blood/substitution fluid mixture from the mixing chamber 140 to the patient. Conduit 142 may therefore be referred to as a bloodline.

For those systems using an occlusive type substitution fluid pump requiring a special single use infusion set (possibly containing a single use sterilization filter), the present invention has the advantage in that a low cost IV administration set or a drip chamber level adjust line can be used instead.

Figure 2:
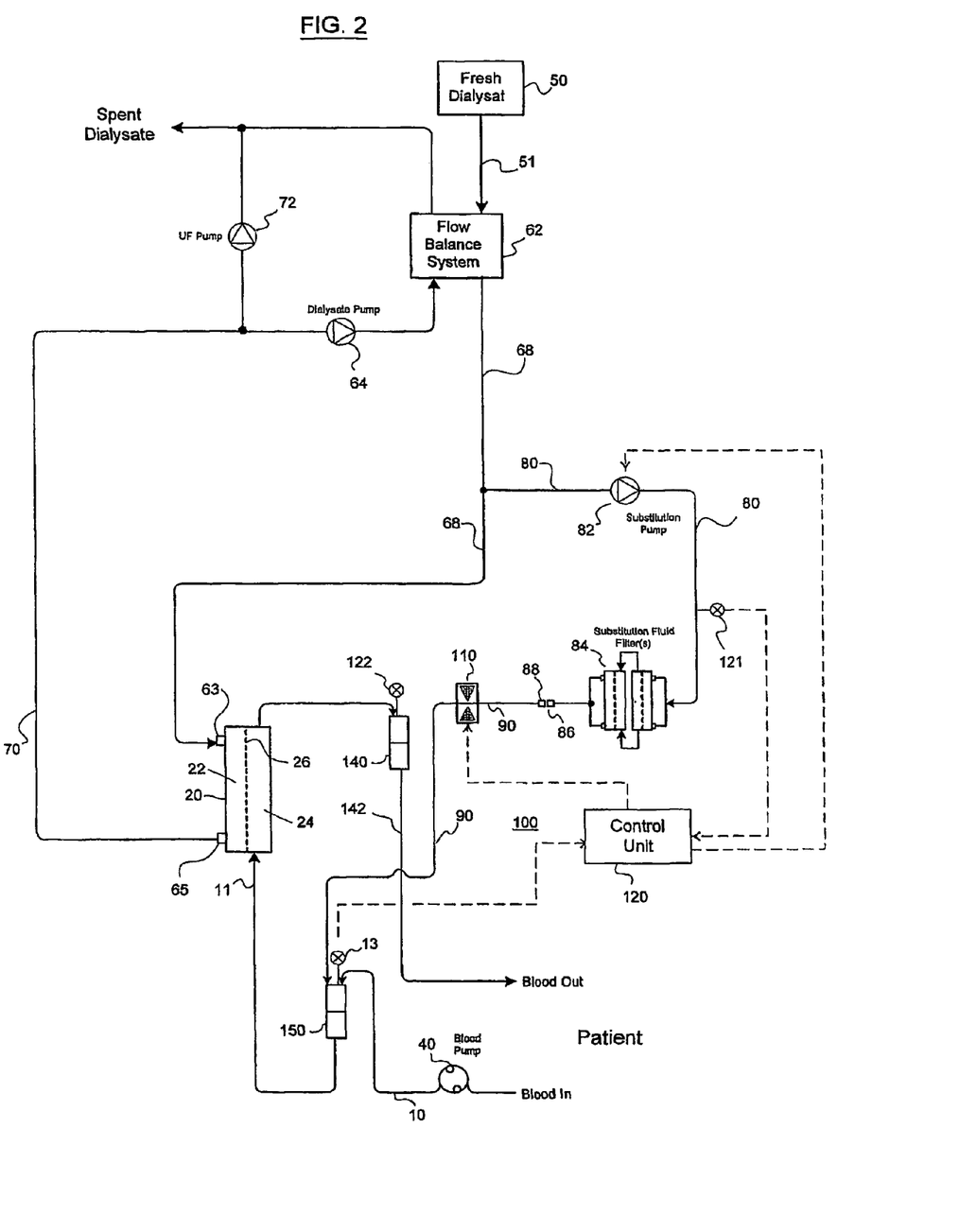
FIG. 2 is a schematic illustration of a fluid sterilization system incorporating a valve mechanism in accordance with a second embodiment.

Reference is made to FIG. 2 which schematically illustrates a second embodiment. In this second embodiment, the present scheme is shown as being part of a substitution fluid delivery system typical of a hemodiafiltration system in which the sterile substitution fluid is introduced into the blood stream in a predilution mode relative to the dialyzer cartridge 20.

In this embodiment, the flexible tubing 90 extends between the connector 88 and a mixing chamber 150 which receives blood through the arterial bloodline 10. Thus, the sterile substitution fluid is delivered to and mixed with blood in the chamber 150 to form a blood/substitution fluid mixture. Preferably, the blood and substitution fluid enter the mixing chamber 150 at one end and a conduit 11 extends from an opposite end of the mixing chamber 150. The conduit 11 is preferably similar to the arterial bloodline 10 and differs in that the conduit 11 carries the blood/substitution fluid mixture from the mixing chamber 150 to the first cartridge 20 (blood compartment 24 thereof).

In this embodiment, the first monitoring device 13 acts as a downstream sensor for monitoring the fluid pressure at downstream locations relative to the pinch valve 110. Preferably, the arterial pressure is also measured at the location of the first monitoring device 13. As with th first embodiment, the fluid pressure of the substitution fluid is continuously monitored at the upstream sensor 121.

In this embodiment, the second monitoring device 122 (i.e. the second sensor) does not serve as a downstream sensor for monitoring the flow pressure of the substitution fluid after the fluid passes through the pinch valve 110 but rather acts as a venous pressure sensor. Sensor 122 thus measures the pressure of the fluid as it enters the chamber 140. Chamber 140 is therefore not a mixing chamber but rather is a chamber which receives the fluid from the dialyzer cartridge 20 and is coupled to conduit 142 which delivers the filtered blood back to the patient. Alternatively, chamber 140 can be eliminated and the filtered blood can simply flow through conduit 142 back to the patient.

In the second embodiment, control of the pinch valve 110 is the same as or similar to the control thereof in the first embodiment in that the pinch valve 110 is designed to prevent retrograde blood flow. More specifically, the pinch valve 110 is opened when the sensed upstream pressure at sensor 121 exceeds the sensed downstream pressure at sensor 13 by a predetermined valve. In the open position, the substitution fluid flows through the pinch valve 110 within the flexible tubing 90 to the mixing chamber 150. In the event that there is a sudden drop in the upstream pressure or a sudden increase in the downstream pressure, the pinch valve 110 is immediately closed to prevent blood and blood proteins from backing up and contaminating the substitution delivery system. After the pinch valve 110 is closed, the substitution pump 82 is stopped to prevent over pressurizing the fluid path between the outlet of the substitution pump 82 and the pinch valve 110. This may be accomplished by sending a signal from the control unit 120 to the substitution pump 82.

Advantageously, the second embodiment prevents retrograde blood flow from the chamber 150 into the flexible tubing 90 which is connected thereto in a pre-dilution scheme. In each embodiment of the present invention, the valve mechanism 100 is easily incorporated into a variety of existing hemodiafiltration apparatus or the like.

Figure 3:
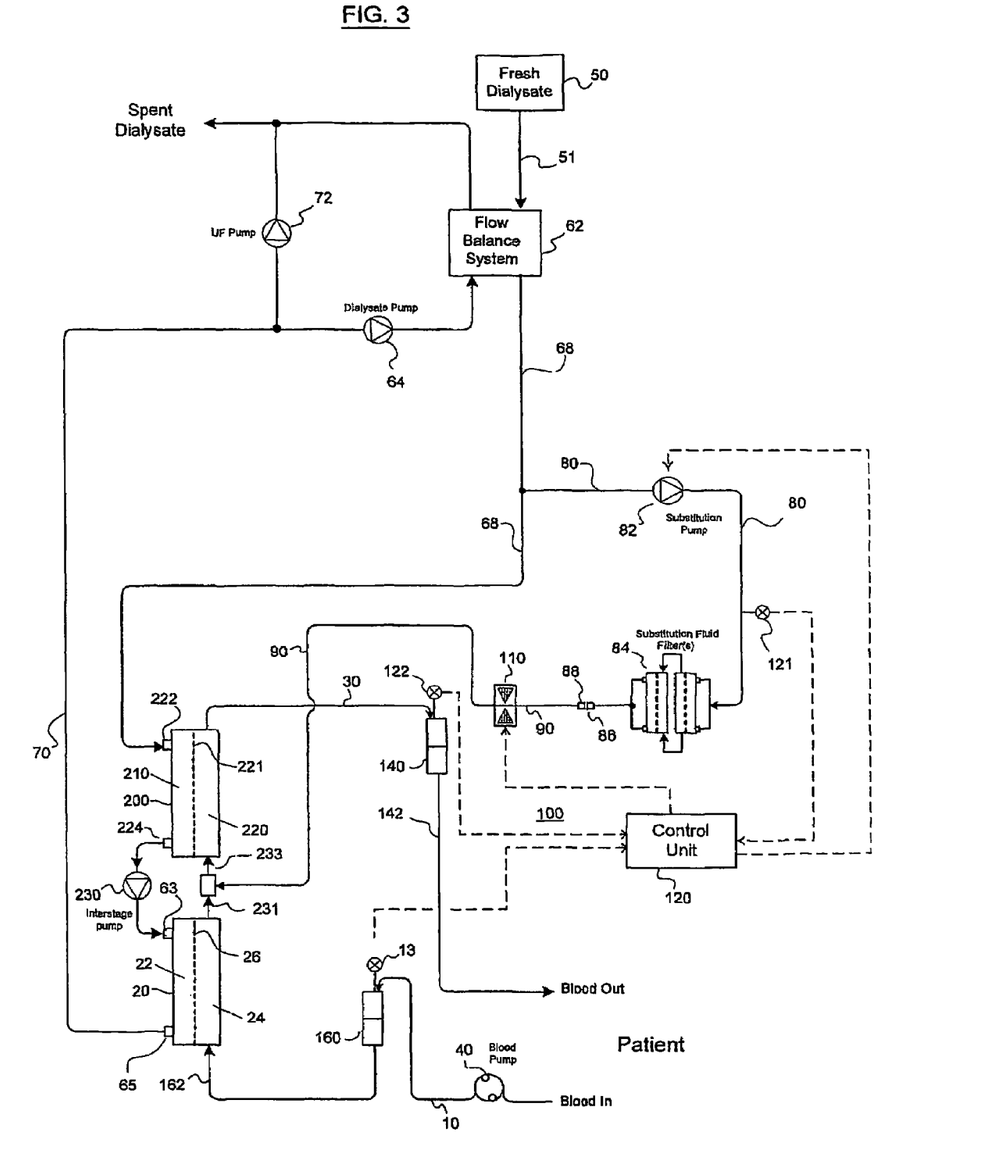
FIG. 3 is a schematic illustration of a fluid sterilization system incorporating a valve mechanism in accordance with a third embodiment of the invention.

Reference is made to FIG. 3 which schematically illustrates a third embodiment of the present invention. In this third embodiment, the present invention is shown as being part of a substitution fluid delivery system typical of a hemodiafiltration system having first and second dialyzer cartridges 20, 200 in which the sterile substitution fluid is introduced at a location between the first and second dialyzer cartridges 20, 200. The substitution fluid can be introduced (i.e., through a connector) into a conduit that extends between and links the first and second dialyzer cartridges 20, 200 or the substitution fluid can be introduced into a chamber that is disposed between the first and second dialyzer cartridges 20, 200 and is connected thereto by one or more conduits.

In this third embodiment, blood is propelled through the extracorporeal circuit using the blood pump 40. The blood flows through the bloodline 10 to the chamber 160. The arterial pressure is measured at the first monitoring device 13 and the measured information is continuously transmitted to the control unit 120. A conduit (bloodline) 162 fluidly connects the chamber 160 to the first dialyzer cartridge 20. The second dialyzer cartridge 200 is similar to the first dialyzer cartridge 20 and may be of any type suitable for hemodialysis, hemodiafiltration, hemofiltration, or heomoconcentration as is the case with the first dialyzer cartridge 20. More specifically, the second dialyzer cartridge 200 has a dialysate compartment 210 and a blood compartment 220 defined by a semipermeable membrane 221. The second dialysate cartridge 200 also includes a dialysate inlet port 222 for receiving a flow of dialysate fluid and a dialysate outlet port 224 which carries spent dialysate fluid from the second dialysate cartridge 200.

The first and second dialysate cartridges 20, 200 are conventionally arranged with the fresh dialysate conduit 68 being connected to the dialysate inlet port 222 so that a portion of the fresh dialysate fluid 50 is delivered to the second dialyzer cartridge 200. After the dialysate fluid flows through the dialysate compartment 210, the dialysate fluid exits the second dialyzer cartridge 200 through the dialysate outlet port 224 and is introduced into the inlet dialysate port 63 of the first dialyzer cartridge 20. Preferably, th dialysate fluid is delivered from the second dialyzer cartridge 200 to the first dialyzer cartridge 20 using a device, such as an interstage pump 230. The dialysate outlet port 65 of the first dialyzer cartridge 20 is connected to the spent dialysate conduit 70 which carries the spent dialysate fluid away as in the other embodiments. The first and second dialyzer cartridges 20, 200 are also arranged so that blood flows from the blood compartment 24 of the first dialyzer cartridge 20 to the blood compartment 220 of the second dialyzer cartridge 200 where it is further filtered.

Similar to the first embodiment, the second dialyzer cartridge 200 is connected to a chamber 140 by the venous bloodline 30. Conduit 142 transports the filtered blood from the chamber 140 back to the patient. The second monitoring device 122, i.e. second sensor, is preferably positioned at the chamber 140 or thereabouts along the venous bloodline 30 so as to monitor the venous pressure of the fluid as it flows through the bloodline 30. The second sensor 122 continuously provides venous pressure data to the control unit 120.

In this embodiment, the substitution fluid is mixed with partially diafiltered blood, denoted 231, between first and second stages of filtering the blood. As used herein, the expression "partially diafiltered blood" refers to blood that has had an amount of toxins removed therefrom using a hemodiafiltration process. The sterile substitution fluid is mixed with the partially diafiltered blood 231 after the blood 231 has been filtered in the first dialyzer cartridge 20 but before the blood 231 is introduced into the second dialyzer cartridge 200. The mixing of the partially diafiltered blood 231 and the substitution fluid forms a blood/substitution fluid mixture, denoted 233. This fluid mixture 233 is then introduced into the blood compartment 220 of the second dialyzer cartridge 200. Preferably, in both the first and second dialyzer cartridges 20, 200, the blood is propelled in a counter-current configuration relative to the flow of the dialysate solution in the dialysate compartments 22, 210. Blood being discharged from the second dialyzer cartridge 200 can be referred to as being diafiltered blood. As used herein, the expression "diafiltered blood" refers to partially diafiltered blood that has been further subjected to a hemodiafiltration process in order to further remove more toxins from the blood.

In the third embodiment, control of the pinch valve 110 is the same as or similar to control thereof in the other embodiment in that the pinch valve 110 is designed to prevent retrograde blood flow. More specifically, the pinch valve 110 is opened when the sensed upstream pressure at sensor 121 exceeds the sensed downstream pressure at a sensor by the predetermined valve. In this embodiment, the downstream pressure may be represented by an average of the arterial pressure measured at the first monitoring device 13 and the venous pressure measured at the second monitoring device 122. In this embodiment, the control unit 120 receives the signals from the respective monitoring devices 13, 122 and generates an average pressure value. Alternatively, the downstream pressure value that is delivered to the control unit 120 can be based on a downstream pressure value at one of the devices 13, 122. In the open position, the substitution fluid flows through the pinch valve 110 within the flexible tubing 90 to the location where it is mixed with the partially diafiltered blood 231 between the first and second filtering stages. In the event that there is a sudden drop in the upstream pressure or a sudden increase in the downstream pressure, the pinch valve 110 is immediately closed to prevent blood and blood proteins from backing up and contaminating the substitution delivery system. After the pinch valve 110 is closed, the substitution pump 82 is stopped to prevent over pressurizing the fluid path between the outlet of the substitution pump 82 and the pinch valve 110. This can be accomplished by sending a signal from the control unit 120 to the substitution pump 82.

The present invention prevents the possibility of retrograde flow from the point of use to the fresh fluid supply path and the fluid supply source and therefore can effectively eliminate the risk of cross contamination that may result when a single fluid source is repeatedly used to treat several patients serially. The present invention is easily incorporated into existing apparatuses. For example, the present invention may be used in conjunction with other system components such as pressure or flow sensors which periodically check system conduit and connection integrity.

It will be appreciated by persons skilled in the art that the present invention is not limited to the embodiments described thus far with reference to the accompanying drawing. Rather the present invention is limited only by the following claims.

What is claimed is:

1. A method of ensuring sterility and preventing contamination of a first fluid delivered through a first conduit from a supply source that contains fresh, unused fluid to a point of use, wherein the first fluid is filtered with a substitution filter assembly before the point of use to produce sterile first fluid, the method comprising: disposing a valve mechanism along the first conduit, the substitution fluid filter assembly being upstream of the valve mechanism, the valve mechanism being positionable between an open position in which the first fluid flows through the first conduit to the point of use and a closed position in which the first fluid is prevented from flowing through the valve mechanism to the point of use; sensing a first flow pressure of the fresh, unused first fluid in the first conduit at a location upstream of the valve mechanism and upstream of the substitution fluid filter assembly; combining sterile, filtered first fluid with a second fluid to form a third fluid at the point of use downstream of the valve mechanism; opening the valve mechanism when the first flow pressure exceeds a reference flow pressure by a predetermined value; and closing the valve mechanism under a preselected condition to prevent the first fluid from flowing to the point of use, the closing of the valve mechanism also preventing retrograde flow of the second and third fluids from the point of use to a location upstream of the valve mechanism, thereby ensuring that the first fluid is sterile and substantially free of contamination, wherein the fluid in the first conduit is divided into a first stream that delivers fresh, unused first fluid to the substitution filter assembly where the first fluid is filtered prior to the point of use and a second stream that delivers the first fluid to a location where the second fluid or the third fluid is dialyzed and the valve mechanism is disposed along the first stream of the first conduit between a location where the first fluid is filtered and the point of use of the sterile first fluid such that the valve mechanism acts on and controls flow of the sterile first fluid in the first conduit downstream of the location where the first fluid is filtered, where a location where the fluid is divided into the first and second streams is located upstream of the valve mechanism and substitution fluid filter assembly such that only the first stream is delivered to the substitution fluid filter assembly.

2. The method of claim 1, wherein the preselected condition is when the first flow pressure decreases an amount over a period of time relative to the reference flow pressure.

3. The method of claim 1, wherein the preselected condition is when the first flow pressure is less than the reference flow pressure.

4. The method of claim 1, further comprising: sensing a second flow pressure of one of the first, second and third fluids at a location downstream of the valve mechanism, the second flow pressure representing the reference flow pressure.

5. The method of claim 4, wherein the valve mechanism is opened when the first flow pressure exceeds the second flow pressure by a predetermined value.

6. The method of claim 4, wherein the preselected condition is when the first flow pressure drops a predetermined amount over a period of time relative to the second flow pressure.

7. The method of claim 4, wherein the preselected condition is when the first flow pressure is less than the second flow pressure.

8. The method of claim 1, wherein the valve mechanism is a pinch valve in communication with a control unit that is communication with a first sensor that senses the first flow pressure, wherein closing the valve mechanism comprises fully occluding the first conduit.

9. The method of claim 1, wherein the point of use comprises a mixing chamber wherein the first fluid is mixed with the second fluid to form the third fluid.

10. The method of claim 1, wherein the second fluid is blood including blood proteins.

11. The method of claim 1, wherein the first fluid is dialysate fluid.

12. The method of claim 1, wherein the first fluid is dialysate fluid, the second fluid is blood, and the third fluid is a mixture of blood and dialysate fluids.

13. The method of claim 1, wherein the apparatus is employed in one of a pre-dilution stage of a hemodiafiltration system, a post-dilution stage of the hemodiafiltration system, and an intermediate stage of the hemodiafiltration system.

14. A safety enhancement for use in an infusion fluid system for delivering and ensuring sterility and preventing contamination of a first fluid along a fluid path from a supply source that contains fresh, unused first fluid to a point of use in the infusion fluid system, the safety enhancement comprising: a first conduit defining the fluid path from the supply source to the point of use, the first conduit having a first branch that delivers fresh, unused first fluid to a location where the first fluid is filtered with a filter assembly and a second branch that delivers fresh, unused first fluid directly to a location where a second fluid or a third fluid is dialyzed, wherein the first conduit is split into the first and second branches at a location upstream of the filter assembly such that only the first fluid in the first branch passes through and is filtered with the filter assembly; a valve mechanism disposed along the first branch of the first conduit between a location where the first fluid is filtered and the point of use of the sterile first fluid such that the valve mechanism controls flow of the sterile first fluid in the first conduit, the valve mechanism being positionable between an open position in which the sterile first fluid flows through the first conduit to the point of use and a closed position in which the sterile first fluid is prevented from flowing through the valve mechanism to the point of use, wherein sterile, filtered first fluid is combined with the second fluid to form the third fluid at the point of use downstream of the valve mechanism; a controller that receives a first control signal representing a flow pressure of the fresh, unused first fluid at a location upstream of the valve mechanism and upstream of the filter assembly, the controller being in communication with the valve mechanism such that the controller opens the valve mechanism by sending an open control signal and closes the valve mechanism by sending a close control signal, the open control signal being sent when the first control signal exceeds a second control signal representing a reference flow pressure, the close control signal being sent under a preselected condition to prevent retrograde flow of one of the second and third fluids to a location upstream of the valve mechanism, thereby ensuring the supply source and an upstream portion of the first conduit remain substantially free of contamination by one of the second and third fluids.

15. The safety enhancement of claim 14, wherein the safety enhancement is employed in an intermediate stage of a hemodiafiltration system having first and second dialyzer cartridges, the first fluid being combined with the second fluid as the second fluid is discharged from the first dialyzer cartridge to form the third fluid that is then introduced into the second dialyzer cartridge.

16. The safety enhancement of claim 14, wherein the preselected condition is when the first control signal decreases a predetermined amount over a period of time relative to the second control signal.

17. The safety enhancement of claim 14, wherein the reference flow pressure is a variable flow pressure value determined by a second sensor that senses one of the first, second, and third fluids at a location downstream of the valve mechanism, and wherein the preselected condition is when the second control signal increases a predetermined amount over a period of time relative to the first control signal.

18. A method of ensuring sterility and preventing contamination of a first fluid delivered through a first conduit from a supply source that contains fresh, unused fluid to a point of use where the first fluid is mixed with a second fluid to form a third fluid, wherein the first fluid is filtered with a substitution filter assembly before the point of use to produce sterile first fluid, the method comprising: disposing a valve mechanism along the first conduit, the substitution fluid filter assembly being upstream of the valve mechanism, the valve mechanism being positionable between an open position in which the first fluid flows through the first conduit to the point of use and a closed position in which the first fluid is prevented from flowing through the valve mechanism to the point of use; sensing a first flow pressure of the fresh, unused first fluid in the first conduit at a location upstream of the valve mechanism and upstream of the substitution fluid filter assembly; combining sterile, filtered first fluid with the second fluid at the point of use to form a third fluid downstream of the valve mechanism; opening the valve mechanism when the first flow pressure exceeds a reference flow pressure by a predetermined value; and closing the valve mechanism under a preselected condition to prevent the first fluid from flowing to the point of use, the closing of the valve mechanism also preventing retrograde flow of the second and third fluids from the point of use to a location upstream of the valve mechanism, thereby ensuring that the first fluid is sterile and substantially free of contamination, wherein the fluid in the first conduit is divided into a first stream that delivers fresh, unused, first fluid to the substitution fluid filter assembly where the first fluid is filtered and then delivered to the point of use and a second stream that delivers the first fluid to a device where the first fluid is used to filter the second fluid or the third fluid and the valve mechanism is disposed along the first stream of the first conduit between a location where the first fluid is filtered and the point of use of the sterile first fluid such that the valve mechanism acts on and controls flow of the sterile first fluid in the first conduit downstream of the location where the first fluid is filtered, where a location where the fluid is divided into the first and second streams is located upstream of the valve mechanism and substitution fluid filter assembly such that only the first stream is delivered to the substitution fluid filter assembly.

* * * * *